United States Patent [19]

Re et al.

[11] 4,001,333
[45] Jan. 4, 1977

[54] PROCESS FOR THE PREPARATION OF DIOLDIONES
[75] Inventors: Luciano Re; Valerio Caciagli, both of Rome, Italy
[73] Assignee: Snamprogetti, S.p.A., Milan, Italy
[22] Filed: June 12, 1975
[21] Appl. No.: 586,357
[30] Foreign Application Priority Data
June 12, 1974 Italy .................. 23897/74
[52] U.S. Cl. .................. 260/586 P; 260/590 R; 260/592; 260/594
[51] Int. Cl.² .................. C07C 45/16; C07C 45/00
[58] Field of Search ....... 260/597 R, 635 H, 593 R, 260/586 P, 590 R, 592, 594
[56] References Cited
UNITED STATES PATENTS

| 2,437,648 | 3/1948 | Mulas .................. | 260/586 P |
|---|---|---|---|
| 2,718,529 | 9/1955 | Smith et al. .................. | 260/635 H |
| 2,773,101 | 12/1956 | Smith et al. .................. | 260/635 H |
| 2,813,130 | 11/1957 | Keeler et al. .................. | 260/586 P |
| 3,317,592 | 5/1967 | MacLeans .................. | 260/590 R |
| 3,337,635 | 8/1967 | Morton et al .................. | 260/594 |
| 3,488,394 | 1/1970 | Cummins et al. .................. | 260/635 H |
| 3,846,478 | 11/1974 | Cummins .................. | 260/635 H |

OTHER PUBLICATIONS
Hofmann, "Ber.", vol. 45, pp. 3329-3336 (1912).
Zelekoff et al., "J.A.C.S.", vol. 72, pp. 5039-5042 (1950).
Re et al., "Helv", vol. 56, pp. 1882-1894 (1973).

Primary Examiner—Norman Morgenstern
Attorney, Agent, or Firm—Ralph M. Watson

[57] ABSTRACT

A dioldione represented by the formula:

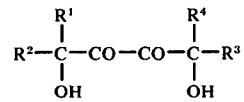

in which $R^1$, $R^2$, $R^3$, $R^4$, the same or different, represent alkyl, cycloalkyl, arylalkyl, aryl or hydrogen, is prepared by reacting a compound represented by the formula:

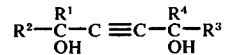

wherein $R^1$, $R^2$, $R^3$, $R^4$ have the above meanings, with an oxidizing mixture consisting of osmium tetroxide and an alkali or alkali-earth metal chlorate.

3 Claims, No Drawings

PROCESS FOR THE PREPARATION OF DIOLDIONES

The present invention relates to a novel process for the preparation of dioldione compounds having the general formula

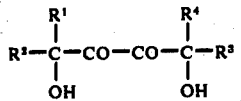

in which $R^1$, $R^2$, $R^3$, $R^4$, the same or different, may be an alkyl, cycloalkyl, arylalkyl, or aryl radical or hydrogen, starting from compounds having the general formula

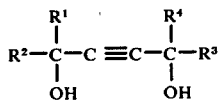

in which $R^1$, $R^2$, $R^3$, $R^4$ have the aforesaid meaning, through a reaction with an oxidizing mixture constituted by osmium tetroxide and an alkali or alkali-earth chlorate.

The dioldione compounds according to the present invention are useful synthesis intermediates, for instance, in the preparation via cyclization of furane derivatives, some of which may be employed as aromatizing agents [for instance, see L. Re, B. Maurer and G. Ohlaff, Helv. 56, 1882 (1973)]. With regard to the known methods for the preparation of the aforesaid dioldione compounds the inventive method has the advantage of being not only less expensive but also simpler from an operating point of view.

Furthermore, in the preparation of furane derivatives through cyclization, the instant synthesis method of the dioldione compounds is particularly interesting since it is possible, through known operations to perform the cyclization on the aqueous end reaction mixture, after the recovery of osmium tetroxide, without isolating the intermediate compound.

According to the inventive process the oxidizing agent is osmium tetroxide which, however, can be used in catalytic amounts (preferably at least 20 mg per g of acetylene compound) it being continuously regenerated from chlorate through an oxidative scission of the adduct between osmium tetroxide and the acetylene compound. Chlorate must, therefore, be present in at least stoichiometric amounts. Moreover osmium tetroxide may be recovered at the end of the reaction either through dragging under a nitrogen stream by catching osmium tetroxide in a trap containing the starting product so as to form the non-volatile adduct or through a selective extraction of osmium tetroxide by means of a suitable solvent (e.g., $CCl_4$, benzene, $Et_2O$) and solvent evaporation after the extract has been added with the starting products, or also through techniques well known to those stilled in the art.

More particularly the oxidation reaction is carried out in an aqueous environment in the temperature range of from 0° to 100° C (generally from +25° to +50° C) and at a pressure which will maintain the system in the liquid phase. When use is made of water insoluble solid substrates we prefer to add an inert usual solvent either miscible and with water and dissolving, at least partially, the substrate (THF, alcohols) or water immiscible dissolving, also only partially, both substrate and osmium tetroxide ($CCl_4$, $Et_2O$, benzene).

The working formalities will be made apparent by the following illustrative examples.

EXAMPLE 1

Preparation of 2,5-dihydroxyhexane — 3,4-dione from 3-hexyn-2,5-diol: to 15 ml of water were added — 2.80 g (22.8 mmoles) of potassium chlorate, 0.050 g (0.197 mmole) of osmium tetroxide and 1.14 g (10.0 mmoles) of 3-hexyn-2,5-diole and the mixture was stirred at room temperature for 18 hours in a closed vessel.

When osmium tetraoxide was to be recovered, it could now be done by bubbling nitrogen through the end reaction vessel, connected at the outlet with a trap provided with a porous septum immersed in dimethylfurane and cooled. Thereby osmium tetroxide, dragged by nitrogen, is caught via hexyndiol adduct formation, which is not volatile. The trap solution could be used, after potassium chlorate addition, for a following preparation. Alternatively, the osmium tetroxide recovery could be carried out by means of selective extraction thereof with $CCl_4$ followed by a dimethylfurane addition to the extract (so as to form adduct) and a solvent distillation; the distillation residue could be employed after an addition of water and potassium chlorate, in a following preparation. The reaction mixture was evaporated to dryness under a 15 mmHg vacuum at room temperature, the residue was repeatedly extracted with an acetone chloroform mixture (1:4) and the extracts, joined together, were dried (anhydrous sodium sulphate) and evaporated to dryness at a bath temperature not higher than 35° C.

1.23 g were obtained (84.5% yield) of 2,5-dihydroxyhexane-3,4-dione, a yellow and very viscous product, having I.R. and NMR spectra agreeing with the known ones (L. Re et al., as abovesaid).

EXAMPLE 2

Preparation of 2,5-dihydroxyheptane-3,4-dione from 3-heptyn-2,5-diol: To 15 ml of water were added 2.80 g (22.8 mmoles) of potassium chlorate, 0.050 g (0.197 mmole) of osmium tetroxide and 1.28 g (10.0 mmoles) of 3-heptyn-2,5-diol, the mixture being stirred at room for 20 hours in a closed vessel.

The reaction mixture was evaporated to dryness under a 15 mmHg vacuum at room temperature, the residue was repeatedly extracted with an acetone-chloroform (1:4) mixture and the extracts, joined together, were dried (anhydrous sodium sulphate) and evaporated to dryness under vacuum at a bath temperature not higher than 35° C. 1.32 g (82.5% yield) of 2,5-dihydroxyheptane-3,4-dione were obtained.

EXAMPLE 3

Preparation of 1,4-dihydroxypentane-2,3-dione from 2-pentyn-1,4-diol. To 15 ml of water were added 2.80 g (22.8 mmoles) of potassium chlorate, 0.050 g (0.197 mmole) of osmium tetroxide and 1.00 g (10.0 mmoles) of 2-pentyn-1,4-diol, the mixture being stirred at room temperature for 17 hours in a closed vessel.

The reaction vessel was evaporated to dryness under a vacuum of 15 mmHg at room temperature, and the residue was repeatedly extracted by an acetone-chloforun (1:4) mixture. The extracts, joined together, were dried (anhydrous sodium sulphate) and evaporated to dryness under vacuum at a bath temperature not higher than 35° C to give 1,4-dihydroxipenten-2,3-dione.

What we claim is:

1. The process of preparing a dioldione compound represented by the formula:

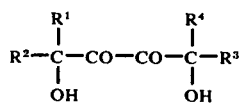

in which $R^1$, $R^2$, $R^3$, $R^4$, the same or different, represent alkyl, cycloalkyl, arylalkyl, aryl or hydrogen, comprising reacting a compound represented by the formula:

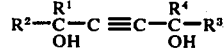

wherein $R^1$, $R^2$, $R^3$, $R^4$ have the above meanings, with an aqueous oxidizing mixture constituted by at least a catalytic quantity of osmium tetroxide and at least a stoichiometric quantity of an alkali or alkali-earth metal chlorate, at a temperature in the range of from 0 to 100° C, and at sufficient pressure to maintain the system in the liquid phase.

2. The process as claimed in claim 1, wherein the reaction is carried out at a temperature in the range of from +25° to +50° C.

3. The process as claimed in claim 1, wherein the reaction is carried out in the presence of water, as such or with an added inert solvent.

* * * * *

UNITED STATES PATENT AND TRADEMARK OFFICE
CERTIFICATE OF CORRECTION

PATENT NO. : 4,001,333
DATED : January 4, 1977
INVENTOR(S) : Luciano Re, Valerio Caciagli It is certified that error appears in the above-identified patent and that said Letters Patent are hereby corrected as shown below:

Column 2, line 2, After "immiscible" insert --and--.

line 9, Correct "to" to read --To-- and delete the dash "-" at the end of the line.

line 46, After "room" insert --temperature--.

line 59, After "diol" insert a colon --:--.

Signed and Sealed this ninth Day of August 1977

[SEAL]

Attest:

RUTH C. MASON
*Attesting Officer*

C. MARSHALL DANN
*Commissioner of Patents and Trademarks*